United States Patent [19]
Kwak et al.

[11] Patent Number: 5,861,158
[45] Date of Patent: Jan. 19, 1999

[54] METHOD AND COMPOSITION FOR TRANSFER OF ACTIVE TUMOR-SPECIFIC IMMUNIZATION FROM AN IMMUNIZED ALLOGENEIC BONE MARROW DONOR

[75] Inventors: Larry W. Kwak, Frederick; Dan L. Longo, Kensington, both of Md.

[73] Assignee: The United States of America as represented by the Deptartment of Health and Human Services, Washington, D.C.

[21] Appl. No.: 153,464

[22] Filed: Nov. 17, 1993

[51] Int. Cl.$^6$ .................. A61K 39/395; A61K 39/00; A61K 39/38; A61K 35/14
[52] U.S. Cl. .................. 424/184.1; 424/130.1; 424/534; 424/277.1; 424/174.1; 424/531
[58] Field of Search .................. 424/88, 531, 277.1, 424/130.1, 174.1, 184.1, 534

[56] References Cited

U.S. PATENT DOCUMENTS

| | | |
|---|---|---|
| 5,126,132 | 6/1992 | Rosenberg . |
| 5,192,537 | 3/1993 | Osband . |
| 5,296,353 | 3/1994 | Ochoa et al. ............ 435/7.23 |
| 5,443,983 | 8/1995 | Ochoa et al. . |
| 5,460,964 | 10/1995 | McGlave . |
| 5,470,730 | 11/1995 | Greenberg . |
| 5,514,364 | 5/1996 | Ildstad . |
| 5,556,763 | 9/1996 | Ochoa et al. . |
| 5,614,610 | 3/1997 | Hellstrom et al. . |
| 5,635,156 | 6/1997 | Ildstad . |

OTHER PUBLICATIONS

Kersey et al, New Eng. J. Med. 317(8): 461–67, 1987.
Meredith et al. Transplantation. 35(4):378–385, 1983.
Lazarus et al, Blood Reviews, 8:169–178, 1994.
Amylon et al, J. Ped. Hematol/Oncol., 19(1):54–61, 1997.
Champlin et al, Acta Hematal. 95:157–163, 1996.
Kwak LW, Campbell MJ, Czerwinski DK, Hart S, Miller RA, Levy R. Induction of immune responses in patients with B–cell lymphoma against the surface immunoglobulin idiotype expressed by their tumors. *N Engl J Med* 327:1209–1215, 1992.
Tura S, Cavo M. Allogeneic bone marrow transplantation in multiple myeloma. *Hematol Oncol Clin North Am*, 6:425–435, 1992.
Attal M, Huguet F, Schlaifer D, Payen C, Laroche M, Fournie B, Mazieres B, Pris J, Laurent G. Intensive combined therapy for previously untreated aggressive myeloma. *Blood*, 79: 1130–1136, 1992.
Campbell MJ, Esserman L, Byars NE, Allison AC, Levy R. Idiotype vaccination against murine B–cell lymphoma. *J Immunol* 145: 1029–1036, 1990.
Kato S, Yabe H, Yabe M, Kimura M, Tsuchida F, Tsuji K, Takahashi M. Studies on transfer of varicella–zoster–virus specific T–cell immunity from bone marrow donor to recipient. *Blood* 75:806–809, 1990.

Campbell MJ, Esserman L, Byars NE, Allison AC, Levy R. Development of a new therapeutic approach to B–cell malignancy: the induction of immunity by the host against cell surface receptor on the tumor. *Int Rev Immunol* 4:251–70, 1989.
Barlogie B, Alexanian, R. Second international workshop on myeloma: Advances in biology and therapy of multiple myeloma. *Cancer Res* 49:7172–7175, 1989.
Kaminski MS, Kitamura K, Maloney DG, Levy R. Idiotype vaccination against murine B–cell lymphoma. Inhibition of tumor immunity by free idiotype protein. *J Immunol* 138: 1289–1296, 1987.
Lum LG, Munn NA, Schanfield MS, Storb R. The detection of specific antibody formation to recall antigens after human bone marrow transplantation. *Blood* 67(3):582–587, 1986.
Lum LG, Seigeuret MC, Storb R. The transfer of antigen–specific humoral immunity from marrow donors to marrow recipients. *J Clin Immunol* 6(5):389–396, 1986.
Wimperis JZ, Prentice HG, Karayiannis P, Brenner MK, Reittie JE, Griffiths PD, Hoffbrand AV. Transfer of a functioning humoral immune system in transplantation of T–lymphocyte–depleted bone marrow. *Lancet*, 1:339–343, 1986.
Milburn GL, Lynch RG. Immunoregulation of murine myeloma in vitro:II. Suppression of MOPC–315 immunoglobulin secretion and synthesis by idiotype specific suppressor T–cells. J Exp Med155:852, 1982.
Kwak et al., "Transfer of Specific Immunity to B–Cell Lymphoma With Syngeneic Bone Marrow in Mice: A Strategy for Using Autologous Marrow as an Anti–Tumor Therapy," *Blood* 78(10):2768–2772 (Nov. 15, 1991).
Kwak et al., "Transfer of Myeloma Idiotype–Specific Immunity From an Actively Immunized Allogeneic Bone Marrow Donor," *Blood* 82(10):200A (Nov. 15, 1993).
Wimperis et al. 1990. Requirements for the Adoptive Transfer of Antibody Response. . . J. Immunol. 144(2):541–7.

*Primary Examiner*—Nita Minnifield
*Attorney, Agent, or Firm*—Needle & Rosenberg, P.C.

[57] ABSTRACT

This invention provides a method of improving a transplantation of hematopoietic cells from a donor to a recipient to treat a hematopoietic cell tumor in the recipient comprising immunizing the donor's hematopoietic cells with an antigen specific for the recipient's hematopoietic cell tumor, and transplanting the donor's immunized hematopoietic cells to the recipient. Also provided is a composition comprising purified hematopoietic cells primed to produce an immunological response to foreign tumor specific antigen. Also provided is a method of treating a tumor by the transplantation of hematopoietic cells from a donor to a recipient to treat the tumor in the recipient comprising immunizing the donor's hematopoietic cells with an antigen specific for the recipient's tumor, and transplanting the donor's immunized hematopoietic cells to the recipient.

17 Claims, No Drawings

METHOD AND COMPOSITION FOR TRANSFER OF ACTIVE TUMOR-SPECIFIC IMMUNIZATION FROM AN IMMUNIZED ALLOGENEIC BONE MARROW DONOR

BACKGROUND OF THE INVENTION

The development of a vaccine against human malignancies has been a long-sought goal which has yet to be achieved. Many of the efforts toward this end have been frustrated by the lack of identification of a tumor-specific antigen which would allow tumor cells to be distinguished from normal cells. Conceptually, such an antigen could be used as a vaccine to induce the host's immune system to reject cells bearing that antigen.

Immunoglobulin (Ig) molecules are composed of heavy and light chains, which possess highly specific variable regions at their amino termini. The variable regions of heavy and light chains combine to form the unique antigen-recognition site of the Ig protein. These variable regions contain determinants (molecule shapes) that can themselves be recognized as antigens, or idiotypes (Id).

B-cell malignancies are composed of clonal proliferations of cells synthesizing a single antibody molecule with unique variable regions in the heavy and light chains. B-cell lymphomas and myelomas are neoplasms of mature lymphocytes which generally express and/or secrete synthesized Ig. The idiotypic determinants of the surface Ig of a B-cell lymphoma or myeloma can thus serve as a tumor-specific marker for the malignant clone.

Studies in experimental animals, as well as in man, have demonstrated the utility of the Ig idiotype as a tumor-specific antigen for the study of the biology of B-cell lymphoma in vitro and as a target for passive immunotherapy in vivo (1–3). Furthermore, active immunization against idiotypic determinants on malignant B-cells has been demonstrated to produce resistance to tumor growth in a number of syngeneic experimental tumor models, as well as specific anti-tumor therapy against established tumors (4–). Furthermore, preclinical studies in subhuman primates demonstrated that optimal immunization with human lymphoma-derived Id required conjugation of the protein to an immunogenic protein carrier (keyhole limpet hemocyanin (KLH)) and emulsification in an adjuvant (15). These results, taken together, provided the rationale for testing autologous tumor-derived idiotypic surface Ig (Id) as a therapeutic "vaccine" against human B-cell malignancies.

The mainstay of therapy for advanced stage myeloma patients with symptoms and signs of progressive disease remains systemic chemotherapy, particularly with alkylating agents and steroids. There is still some controversy regarding the superior efficacy of multiagent intensive chemotherapy regimens, such as the M2 or alternating combination chemotherapy regimens described by the Southwest Oncology Group and Medical Research Council, but most randomized trial results demonstrate only a modest incremental advantage in long-term overall survival compared with standard melphalan and prednisone, with no significant numbers of long-term disease-free survivors (16–23). Thus, although partial remissions of up to 60% are obtained with a variety of regimens, the median survival of about 30 months has remained constant for the last 30 years.

A more aggressive approach with intensive high dose chemoradiotherapy with either autologous or allogeneic bone marrow transplantation (BMT) is currently being explored by several groups of investigators. These protocols have improved initial response rates, although it remains to be seen whether these remissions are maintained with longer follow-up periods (24–28). Regardless of the initial responsiveness rates, the vast majority (>90%) of patients currently treated by these methods experience an eventual relapse of the tumor.

Many groups have described monoclonal B-cell populations in the peripheral blood as well as in the bone marrow of patients with myeloma, and these cells bear the myeloma protein idiotype on their surface as evidence of the clonal identity with the malignant plasma cells (29–37). As the removal of malignant plasma cells by chemotherapy does not appear to deplete the malignant stem cell (38), eradication of these precursor B-cells may ultimately be necessary for successful treatment of this disease.

The goal of the specific strategy described herein was to attempt to transfer tumor antigen-specific immunity induced in a bone marrow donor to a sibling BMT recipient with myeloma, as a means to enhance the therapeutic efficacy of allogeneic BMT. The transfer of induced antigen-specific humoral immunity to viral and other pathogens from immune donors has been explored in BMT patients as a potential therapeutic approach to the problem of increased host susceptibility to infection following the BMT procedure (39–42). A recent report also suggested the possible transfer of Varicella Zoster Virus specific cellular immunity from immune marrow donors to BMT recipients (43). This report, however, was inconclusive as to the origin of the cellular immunity response due to the immunization of both the donor and the recipient. Moreover, the literature reports that transfer of specific cellular immunity cannot be achieved in the context of transplantation (40).

Until this invention only a small percentage (<10%) of investigators had succeeded in eradicating a myeloma through BMT. This percentage is even smaller in the case of patients in the advanced stages of myeloma. The literature does not show that an immune response, and specifically a cellular immune response to a tumor specific antigen, could be transferred exclusively from an immunized donor in a BMT. Thus, donor immunization with myeloma Id represents a very important strategy for enhancing the specific anti-tumor effect of allogeneic marrow grafts.

SUMMARY OF THE INVENTION

The present invention provides a method of improving a transplantation of hematopoietic cells from a donor to a recipient to treat a hematopoietic cell tumor in the recipient comprising immunizing the donor's hematopoietic cells with an antigen specific for the recipient's hematopoietic cell tumor and transplanting the donor's immunized hematopoietic cells to the recipient. The donor's transplanted hematopoietic cells improve the transplantation of the hematopoietic cells to treat the hematopoietic cell tumor in the recipient.

Additionally, the invention provides a composition comprising purified hematopoietic cells primed to produce an immunological response to foreign tumor specific antigen.

DETAILED DESCRIPTION OF THE INVENTION

The present invention provides a method of improving a transplantation, ie. an adoptive transfer, of hematopoietic cells from a donor to a recipient to treat a hematopoietic cell tumor in the recipient comprising immunizing the donor's hematopoietic cells with an antigen specific for the recipient's hematopoietic cell tumor and transplanting the donor's immunized hematopoietic cells to the recipient. The donor's transplanted hematopoietic cells improve the transplantation of the hematopoietic cells to treat the hematopoietic cell tumor in the recipient. Moreover, the method transfers antigen-specific antitumor immunity from an immunized donor to the recipient. Thus, the treatment of any tumor which is treated by donor to recipient hematopoietic cell transplantation can be enhanced using this invention.

Additionally, the invention provides a composition comprising purified hematopoietic cells primed to produce an immunological response to foreign tumor specific antigen. As used herein, "purified" means substantially removed from the presence of naturally occurring proteins, cells or tissues with which the antigens naturally occur. As also used herein "foreign" means the cells are primed to an antigen introduced from a non-self source. The foreign tumor specific antigen can, for example, be derived from an allogeneic tumor, an isogeneic tumor, a syngeneic tumor, or a xenogenic tumor. Therefore, the immunological response can be obtained, for example, from a tumor of an individual of the same species. For example, the tumor can be obtained from a sibling.

In a preferred embodiment the invention also provides that the hematopoietic cells can be T-cell precursors. T-cell precursors contemplates undifferentiated or immature hematopojetic cells which will mature into immunologically competent T-cells. In a more preferred embodiment the hematopoietic cells are bone marrow cells.

The invention also provides that the immunological response to which the cells are primed is a proliferation of peripheral blood mononuclear cells. The invention also contemplates that the immunological response is the production of anti-tumor specific antigen antibodies and cellular immune responses. Furthermore, additional genes, such as those encoding for growth factors, may be introduced into the donor's immunized hematopoietic cells to enhance the immunological response and effectiveness of the present method and composition.

The appropriate tumor specific antigen used in the donor immunization naturally depends on the tumor type being treated. For example, when the tumor is a B-cell myeloma the tumor specific antigen can comprise an immunoglobulin idiotype. This immunoglobulin idiotype can, for example, further comprise the entire immunoglobulin molecule, a Fab, F(ab)$_2$, or the like. For example, the immunoglobulin idiotype can be IgG kappa.

The present invention contemplates the use of various other hematopoietic tumor cell specific antigens. For example, Ras oncoproteins and p53 from leukemia cells may be used to immunize the donor. The present invention contemplates immunizing the donor's hematopoietic cells against solid tumor specific antigens. Such examples of solid tumor specific antigens include carcino-embryonic antigen (CEA) from a colon tumor, Raf oncoprotein from an adenocarcinoma, and GD2 and GD3 from a melanoma. The effectiveness of the particular antigen can be determined following the methods set forth in the Example.

Tumor specific antigens can be obtained, for example, through isolation and purification of immunoglobulins, or immunogenic portions thereof, from naturally occurring B-cell surfaces or from blood plasma. For example, whole cells can be irradiated, sonicated and centrifuged to yield plasma suspended immunoglobulins. The immunoglobulins can be produced either in vivo or in vitro. The immunoglobulins can be produced by growth stimulated cells, genetically engineered cells, or monoclonal antibody producing hybridoma cells. For example, the idiotype can be identified or produced through the use of regional consensus primers and PCR amplification and/or cloning followed by gene expression.

Non-idiotype containing antigens can be obtained following known procedures or are commercially available. See generally, *The Oncogene Handbook*, T. Curran, E. P. Reddy, and A. Salka (ed.), Elsevier Science Publishers, The Netherlands (1988). Alternatively, appropriately treated, such as by irradiation, whole tumor cells may be used to comprise a tumor specific antigen. Furthermore, the donor's hematopoietic cells may be genetically engineered or recombined with genes encoding other immunological stimulants, such as cytokines, to enhance the present methods and compositions.

In a preferred embodiment, the invention provides that the tumor specific antigen can be conjugated to an immunogenic molecule, for example keyhole limpet hemocyanin (KLH). Other suitable immunogenic molecules include heat shock proteins, cholera toxin, bovine serum albumin, tetanus toxoid, thyroglobulin, and cytokine molecules. The immunogenic molecule can be optimized using standard immunological techniques. Such immunogenic molecules can be conjugated using standard techniques.

In a further preferred embodiment, an adjuvant is administered with the antigen, for example SYNTEX adjuvant formulation 1 (SAF-1) composed of 5 percent (wt/vol) squalane (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trealose dimycolate and cell wall skeleton (MPL+TDM+CWS) in 2% squalene/Tween 80 emulsion. The effectiveness of an adjuvant may be determined by measuring the immune response directed against the antigen using standard procedures.

Furthermore, the invention provides that the hematopoietic cell tumor can be a B-cell or T-cell malignancy, eg. a myeloma, a lymphoma or a leukemia. A B-cell or T-cell malignancy contemplates a monoclonal gammopathy of undetermined significance (MGUS) and premalignancy conditions.

In a preferred embodiment, the donor's hematopoietic cells are bone marrow cells. However, the donor's hematopoietic cells may also be peripheral or lymphoid cells. These peripheral or lymphoid cells can be obtained for example from the blood through leukapheresis.

The donor's hematopoietic cells may be immunized against the recipient's tumor specific antigen either in vivo or in vitro. The in vitro immunization may be accomplished, for example, by exposing the donor's cells to tumor specific antigen in a culture plate (14).

The immunogenic composition can be administered to the donor orally, parenterally (e.g., intravenously), by intramuscular injection, by intraperitoneal injection, topically, transdermally, or the like, although subcutaneous injection is typically preferred. Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined. (Arnon, R. (Ed.) *Synthetic Vaccines* I:83–92, CRC Press, Inc., Boca Raton, Fla., 1987). The exact amount of such compounds required will vary from subject to subject, depending on the species, age, weight and general condition of the subject, the severity of the disease that is being treated, the particular compound used, its mode of administration, and the like. Thus, it is not possible to specify an exact amount. However, an appropriate amount may be determined by one of ordinary skill in the art using only routine experimentation given the teachings herein.

Generally, the dosage will approximate that which is typical for the administration of vaccines, and will be in the range of about 5 to 1000 ug/dose, and preferably in the range of 50 to 500 ug/dose. The number of doses is in the range of 1 to 10, and preferably in the range of 2 to 5. The frequency of dosages for immunization of the donor is in the range of 1 to 10 weeks, and preferably in the range of 2 to 4 weeks. The time elapsed after donor immunization until administration to the recipient is in the range of 1 day to 10 weeks, and preferably in the range of 2 to 4 weeks.

The compositions, as noted above, will include, as noted above, an effective amount of the selected antigen in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected antigen without causing any undesirable biological effects or interacting in a deleterious manner with any of the other components of the composition in which it is contained. Actual methods of preparing such dosage forms are known, or will be apparent, to those skilled in this art; for example, see *Remington's Pharmaceutical Sciences* (45).

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

EXAMPLES

Transfer of Myeloma Tumor-Specific Immunity from an Actively Immunized Allogeneic Bone Marrow Donor Isolation and Conjugation of Myeloma Idiotype Protein.

Process Overview. Since a B-cell malignancy myeloma expresses a unique idiotype, the vaccine must be developed on a customized basis from the plasma of each myeloma patient which contains Id in large quantities. The isotype of the circulating paraprotein for this patient was IgG kappa.

Purification of Idiotype

Water Dialysis. As an initial purification and concentration step, plasma containing myeloma Id was dialyzed against sterile water for injection (WFI). The resultant reduction in salt concentration in the plasma caused preferential precipitation of immunoglobulin. The resulting precipitate was collected by centrifugation and resuspended in an appropriate volume of 0.01M Tris.

DEAE Chromatoaraphy. A DEAE Chromatography gel, DE 52, was immersed in 0.5M NaOH and washed 3 times with WFI. The DE 52 gel was then stirred into an equal volume of 0.1M Tris, and the step was repeated until the resulting supernatant had the required pH of 8±0.2 and conductivity (±0.02 mMhos) of the starting buffer. The gel was then equilibrated with 0.01M Tris and packed into a column.

The actual chromatography procedure was performed at 4° C. in an environmentally controlled cold room. The concentrated plasma precipitate was loaded onto the DE 52 column and washed with two gel volumes of 0.01M Tris. The Id was eluted with a stepwise gradient from 0.01M Tris, pH 8.0 (±0.2) to 0.1M Tris, pH 8.0 (±0.2), using absorption at 280 nm to monitor the protein effluent. The protein peak was collected in 1 ml fractions, and based on SDS-PAGE, selected fractions were pooled.

Sodium Sulfate Precipitation. In a laminar flow hood in the clean room, the selected pooled fractions were transferred to sterile pre-rinsed dialysis tubing and dialyzed against 10 volumes of 20% $Na_2SO_4$ for 16–20 hours. When dialysis was complete, the dialysate was aseptically transferred to sterile centrifuge tubes and the precipitate collected by centrifugation. The pellet was resuspended in sterile 0.9% normal saline. The resuspended pool was then dialyzed against 20 volumes of 0.9% normal saline for 16–20 hours. The final material was filtered through a 0.2 micron filter and adjusted to a final concentration of 1 mg/ml.

Conjugation of Idiotype to KLH

Preparation of KLH. KLH was obtained from Calbiochem, San Diego, Calif. (Cat. #374805). The KLH was supplied in a lyophilized form containing more than 60% protein in BES buffer and magnesium sulfate. The protein purity, which is determined by the vendor, was greater than 90%.

Prior to conjugation, the KLH was passed over a Pyrosorb endotoxin removal matrix (Cuno, Inc., Cat. #7503101 PS). The binding capacity of the support is >$10_7$ EU endotoxin per cartridge. Repeated passage of the KLH over the columns reduced the endotoxin to an acceptable level. The gel was regenerated with 1.0M NaOH.

Conjugation of Idiotype to KLH. Equivalent amounts of Id and KLH (equal weights and volumes) were mixed together, and glutaraldehyde, (Sigma, St. Louis, Mo.) was added to a final concentration of 0.1%. The mixture was slowly stirred for 4 hours at room temperature. A 1.0M glycine in PBS solution was added to the mixture to a final concentration of 0.1M glycine to block residual glutaraldehyde, and the mixture was stirred an additional 15 minutes. Unconjugated glycine and glutaraldehyde were removed by dialysis in sterile sodium chloride for injection, USP.

Vialing. The final product was aseptically filled into sterile depyrogenated containers under a laminar flow hood. The final fill volume to be delivered was 1 ml which yielded a patient dose of 0.5 mg of Id.

Pluronic Polymer-Based Adjuvant

Id-KLH was mixed with a Pluronic polymer-based adjuvant. This vehicle formulation contains materials already authorized for use in pharmaceutical and cosmetic formulations and had been shown to be safe in the 12 patients observed in the phase I trial (15). The components were 5% squalane (w/v), 2.5% Pluronic L121 and 0.2% Tween-80 in phosphate buffered saline. All three components were obtained from commercial vendors and were sterilized by filtration or autoclaving before use.

The Pluronic polymer-based adjuvant was prepared 24 hours in advance of each immunization, and each lot was tested for sterility. One ml of adjuvant was produced by mixing Tween (0.4%)/PBS (0.85 ml), L121 (0.05 ml), and squalane (0.1 ml) to produce an emulsion. Immediately prior to vaccination of the donor, this emulsion was mixed (vortexed) with 1 ml Id-KLH to produce a final injection volume of 2 ml.

Immunization and Transfer of Immunity

The BMT donor was a healthy 47 year-old white male sibling whose human lymphocyte antigens HLA type was identical to that of the patient. The patient (BMT recipient) was a 45 year old woman, who was previously noted in April of 1987 to have an increased total protein. Two years later she was noted to have a monoclonal protein of 2.4 grams on serum protein electrophoresis and 12% plasma cells in the marrow. By immunofixation the protein was monoclonal IgG kappa. Skeletal survey was normal and plasma cell labeling index was less than 1%. A diagnosis of monoclonal gammopathy of undetermined significance (MGUS) was made. No treatment was given, but by fall of 1991 she began to note back pain and the IgG level had risen to 4.2 grams per deciliter. Treatment was not initiated until fall of 1992 when a skeletal survey was done demonstrating multiple lytic lesions involving the lumbar spine, pelvis and proximal femurs. At that time the IgG level had risen to 4.5 grams per deciliter. She received local radiation therapy in December of 1992 from T4 to T7, total dose 2600 cGy. In January of 1993 therapy with VAD was initiated but because of the development of ileus, vincristine was deleted and she received two more cycles of adriamycin and dexamethasone. Although there was a modest reduction in the monoclonal protein to a level of 3.1 grams, back and pelvic pain increased dramatically. The patient was given a cycle of thioTEPA 100 mg/m$^2$ and received 2200 cGy irradiation from T2 to T6. In February of 1993 there was modest pain improvement but the M protein spike increased to 3.9 grams per deciliter.

The HIA identical brother was identified and the patient was transferred to Fred Hutchinson Cancer Research Center in Seattle, Washington for further treatment. The 47 year-old male HLA-matched sibling donor was immunized with two s.c. injections of 0.5 mg myeloma IgG, purified from the plasma of the BMT recipient, conjugated to keyhole limpet hemocyanin (KLH), and emulsified in the previously described Pluronic polymer-based adjuvant, at one week intervals before bone marrow transplantation (BMT). The injections were administered on March 30 and Apr. 6, 1993. Donor toxicity consisted only of mild reactions at injection sites. Successful donor immunization was demonstrated by serum antibodies which bound specifically to patient-derived myeloma IgG and specific proliferation of peripheral blood mononuclear cells (PBMC) to the IgG in vitro.

On the fifth of April, the patient began a bone marrow transplant conditioning regimen consisting of busulfan 3.5 mg/kg/day in four divided doses given daily for four consecutive days followed by cyclophosphamide 50 mg/kg per day intravenously over three consecutive days. After one day of rest, bone marrow from the immunized, HLA identical brother was infused. The nucleated cell count per kilogram body weight was $3.4 \times 10^8$. GVHD (graft-vs.-host disease) prophylaxis consisted of methotrexate given on days 1, 3, 6 and 11 and cyclosporine 3 mg/kg beginning on day 1 and continuing through day 150. The patient was herpes simplex and cytomegalovirus sero-positive and was given acyclovir prophylaxis 250 mg/m$^2$ intravenously q12 hours and weekly intravenously immunoglobulin 500 mg/kg. The patient was in poor physical condition and was essentially bed ridden from mid-January 1993 until mid-July 1993. The early post-transplant course was complicated by urine culture that was culture positive for coagulase negative staphylococcus on Apr. 16, 1993, requiring treatment with clindamycin. Engraftment to a neutrophil count greater than 500/$\mu$l, occurred on day 14 and platelet transfusion independence on day 21. Skin rash developed on approximately day 28 and required the addition of prednisone 2 mg/kg added to the cyclosporine on day 40. On day 38 the patient was transferred out of the bone marrow transplant unit to the intermediate care unit for rehabilitation.

The BMT recipient was a 45 year-old white female with advanced refractory myeloma (multiple bony lesions, 50% marrow plasma cells, and 3.9 gm/dl M-protein) progressing on therapy. Analysis of her pre-BMT serum and PBMC, respectively, revealed no detectable humoral or lymphoproliferative response to autologous IgG idiotype. Engraftment was normal and accompanied by grade 2 skin GVHD responsive to therapy. 60 days post-BMT, recipient PBMC proliferated both to the KLH control protein (stimulation index [S.I.] 48.3 at 50 mcg/ml) and to Id (S.I. 4.8) when assayed independently in 5 day in vitro cultures. An Id-specific T-cell line has also been established from recipient PBMC. Specificity was demonstrated by the lack of proliferation to a panel of isotope-matched Ig of unrelated idiotypes. No humoral anti-idiotypic response has been detected in the recipient. The recipient demonstrated an ongoing clinical response, including declining M-protein, 0.4 gm/dl, and absence of dysplastic marrow plasma cells at day 100. As of mid-November of 1993, no myelomic relapse had been detected in the recipient.

The preceding examples are intended to illustrate but not limit the invention. While they are typical of those that might be used, other procedures known to those skilled in the art may be alternatively employed.

Throughout this application various publications are referenced by numbers. Following is a complete citation to the publications. The disclosures of these publications in their entireties are hereby incorporated by reference into this application in order to more fully describe the state of the art to which this invention pertains.

REFERENCES

1. Stevenson, G T, Stevenson F K. Antibody to molecularly defined antigen confined to a tumor cell surface. *Nature*, 1975, 254:714–6.
2. Stevenson G T, Elliott E V, Stevenson F K. Idiotypic determinants on the surface immunoglobulin of neoplastic lymphocytes: a therapeutic target. *Fed Proc*, 1977, 36:2268–71.
3. Miller R A, Maloney D G, Warnke R, Levy R. Treatment of B-cell lymphoma with monoclonal anti-idiotype antibody. *N Engl J Med*, 1982, 306:517–22.
4. Sirisinha S, Eisen HN. Autoimmune-like antibodies to the ligand-binding sites of myeloma proteins. *Proc Natl Acad Sci USA*, 1971, 68:3130–5.
5. Jorgensen T, Gaudernack G, Hannestad K. Immunization with the light chain and the VL domain of the isologous myeloma protein 315 inhibits growth of mouse plasmacytoma MOPC-315. *Scand J Immunol*, 1980, 11:29–35.
6. Daley M J, Gebel H M, Lynch R G. Idiotype-specific transplantation resistance to MOPC-315: Abrogation by post-immunization thymectomy. *J Immunol*, 1978, 120:1620–4.
7. Bridges S H. Participation of the humoral immune system in the myeloma-specific transplantation resistance. *J Immunol*, 1978, 121:479–83.
8. Freedman P M, Autry J R, Tokuda S, Williams R C, Jr.

Tumor immunity induced by preimmunization with BALB/c mouse myeloma protein. *J Natl Cancer Inst*, 1976, 56:735–740.
9. Sugai S, Palmer D W, Talal N, Witz I P. Protective and cellular immune responses to idiotypic determinants on cells from a spontaneous lymphoma of NZB/NZWF1 mice. *J Exp Med*, 1974, 140:1547–58.
10. Stevenson F K, Gordon J. Immunization with idiotypic immunoglobulin protects against development of B lymphocytic leukemia, but emerging tumor cells can evade antibody attack by modulation. *J Immunol* 1983, 130:970–973.
11. George A J T, Tutt A L, Stevenson F K. Anti-idiotypic mechanisms involved in the suppression of a mouse B-cell lymphoma, B C $L_1$. *J Immunol* 1987, 138:628–634.
12. Kaminski M S, Kitamura K, Maloney D G, Levy R. Idiotype vaccination against murine B-cell lymphoma. Inhibition of tumor immunity by free idiotype protein. *J Immunol*, 1987, 138:1289–1296.
13. Campbell M J, Esserman L, Byars N E, Allison A C, Levy R. Idiotype vaccination against murine B-cell lymphoma. *J Immunol*, 1990, 145:1029–1036.
14. Kwak L W, Campbell M J, Czerwinski D K, Hart S, Miller R A, Levy R. Induction of immune responses in patients with B-cell lymphoma against the surface immunoglobulin idiotype expressed by their tumors. *N Engl J Med*, 1992, 327:1209–1215.
15. Campbell M J, Esserman L, Byars N E, Allison A C, Levy R. Development of a new therapeutic approach to B-cell malignancy: the induction of immunity by the host against cell surface receptor on the tumor. *Int Rev Immunol*, 1989, 4:251–70.
16. Oken M M, Tsiatis A, Abramson N et al. Comparison of MP with intensive VBMCP therapy for the treatment of multiple myeloma (MM) (abstr.) *Proc Am Soc Clin Oncol*, 1984, 3:270.
17. Pavlovsky S, Saalavsky J, Tezanos P M, et al. A randomized trial of melphalan and prednisone versus melphalan, prednisone, cyclophosphamide, MeCCNU, and vincristine in untreated multiple myeloma. *J Clin Oncol*, 1984, 2:836–840.
18. Hansen O P, Clausen N T, Drivsholm A, et al. Phase II study of intermittent 5-drug regimen (VBCMP) versus intermittent 3-drug regimen (VMP), versus intermittent melphalan and prednisone (MP) in myelomatosis. *Scand J Haematol*, 1985, 35:518–524.
19. Palva I P, Ahrenberg A, Almquist K, et al. Aggressive combination chemotherapy in multiple myeloma. A multicentre trial. *Scand J Haematol*, 1985, 35:205–209.
20. Kildahl-Anderson P, Bjark P, Bondevik A, et al. Multiple myeloma in central Norway 1981-1982: A randomized clinical trial of 5-drug combination therapy versus standard therapy. *Scand J Haematol*, 1986, 37:243–248.
21. Durie B G M, Dixon B, Carter S, et al. Improved survival duration with combination chemotherapy induction for multiple myeloma: A Southwest Oncology Group study. *J Clin Oncol*, 1986, 4:1127–1237.
22. MacLennon I C M, Kelly Krys R A, Crockson E H, et al. Results of the MRC myelomatosis trials for patients entered since 1980. In Proceedings of British Myeloma Workshop, Blenheim Palace, London, England, October 14–16, 1987.
23. Blade J, Miguel J S, Alcala A, et al. A randomized multicentric study of comparing alternating combination chemotherapy (VCMP/VBAP) and melphalan-prednisone in multiple myeloma. *Blut*, 1990, 60:319–322.
24. Gahrton G, Tura S, Ljungman P, et al. Allogeneic bone marrow transplantation in multiple myeloma using HLA-compatible sibling donors-an EBMT Registry Study. *Bone Marrow Transplant*, 1991, 7 Suppl. 2:32.
25. Gahrton G, Tura S, Ljungman P, et al. Allogeneic bone marrow transplantation in multiple myeloma, European Group for Bone Marrow Transplantation. *N Enql J Med*, 1991, 325:1267–1273.
26. Angelucci E, Baronciani D, Lucarelli G, Galimberti M, Polchi P, Filippetti A, Filocamo M, Donati M. Long-term complete remission after allogeneic bone marrow transplantation in multiple myeloma. *Bone Marrow Transplant*, 1991, 8:307–309.
27. Attal M, Huguet F, Schlaifer D, Payen C, Laroche M, Fournie B, Mazieres B, Pris J, Laurent G. Intensive combined therapy for previously untreated aggressive myeloma. *Blood*, 1992, 79:1130–1136.
28. Topolsky D, Crilley P, Leasure N, Bulova S, Lrodsky I. Syngeneic marrow transplantation in multiple myeloma. *Leuk Res*, 1992, 16:415–416.
29. Abdou N I, Abdou N L. The monoclonal nature of lymphocytes in multiple myeloma. Effects of therapy. *Ann Intern Med*, 1975, 83:42.
30. Kubagawa H, Volger L, Capra J H D, et al. Studies on the clonal origins of multiple myeloma. Use of individually specific (idiotype) antibodies to trace the oncogenic event to its earliest point of expression in B-cell differentiation. *J Exp Med*, 1979, 150–792.
31. Bast E, van Camp B, Reynaert P, et al. Idiotypic peripheral blood lymphocytes in monoclonal gammopathy. *Clin Exp Immunol*, 1982, 47:682.
32. Mellstedt H, Holm G, Pettersson D, et al. Idiotype bearing lymphoid cells in plasma cell neoplasia. *Clin Haematol*, 1982, 11:65.
33. Berenson J, Wong R, Kim K, et al. Evidence for peripheral blood B lymphocyte but not T lymphocyte involvement in multiple myeloma. *Blood*, 1987, 70:1550.
34. Boccadoro M, Omede P, Massaia M, et al. Human myeloma: Several subsets of circulating lymphocytes express plasma cell-associated antigens. *Eur J Haematol*, 1988, 40:299.
35. King M A, Nelson D S. Tumor cell heterogeneity in multiple myeloma: Antigenic, morphologic and functional studies of cells from blood and bone marrow. *Blood*, 1989, 73:1925.
36. Jensen G S, Mant M J, Belch A G, et al. Selective expression of CD45 isoforms defines CALLA+ monoclonal B lineage cells in peripheral blood from myeloma patients as late stage B-cells. *Blood*, 1991, 78:711.
37. Pilarski L M, Jensen G S. Monoclonal circulating B-cells in multiple myeloma. A continuously differentiating, possible invasive, population as defined by expression of CD45 isoforms and adhesion molecules. *Hematol Oncol Clin North Am*, 1992, 6:297–322.
38. Barlogie B, Alexanian, R. Second international workshop on myeloma: Advances in biology and therapy of multiple myeloma. *Cancer Res*, 1989, 49:7172.
39. Starling K A, Falletta J M, Fernback D J. Immunologic chimerism evidence of bone marrow graft acceptance in an identical twin with acute lymphocytic leukemia. *Exp Hematol*, 1975, 3:244.
40. Lum L G, Munn N A, Schanfield M S, Storb R. The detection of specific antibody formation to recall antigens after human bone marrow transplantation. *Blood*, 1986, 67:582.
41. Lum L G, Seigeuret M C, Storb R. The transfer of antigen-specific humoral immunity from marrow donors to marrow recipients. *J Clin Immunol*, 1986, 6:389.
42. Wimperis J Z, Prentice H G, Karayiannis P, Brenner M K, Reittie J E, Griffiths P D, Hoffbrand A V. Transfer of a functioning humoral immune system in transplantation of T-lymphocyte-depleted bone marrow. *Lancet*, 1986, 1:339.

43. Kato S, Yabe H, Yabe M, Kimura M, Ito M, Tsuchida F, Tsuji K, Takahashi M. Studies on transfer of varicella-zoster-virus specific T-cell immunity from bone marrow donor to recipient. *Blood*, 1990, 75:806.

What is claimed is:

1. A method of improving a transplantation of hematopoietic cells from a human donor to an allogeneic recipient to enhance cellular immunity to treat a hematopoietic cell tumor in the recipient comprising:
   a. immunizing the donor's hematopoietic cells with an antigen specific for the recipient's hematopoietic cell tumor; and
   b. transplanting the donor's immunized hematopoietic cells directly to the recipient, such that an antigen specific effector T cell immune response to the hematopoietic cell tumor is transferred to the recipient, the donor's transplanted and immunized hematopoietic cells thereby improving the transplantation of the hematopoietic cells to treat the hematopoietic cell tumor in the recipient.

2. The method of claim 1, wherein the antigen comprises an immunoglobulin idiotype.

3. The method of claim 2, wherein the immunoglobulin idiotype further comprises the entire immunoglobulin molecule.

4. The method of claim 2, wherein the immunoglobulin idiotype is an IgG kappa.

5. The method of claim 1, wherein the antigen is conjugated to an immunogenic molecule.

6. The method of claim 5, wherein the immunogenic molecule is keyhole limpet hemocyanin.

7. The method of claim 1, wherein an adjuvant is administered with the antigen.

8. The method of claim 1, wherein the hematopoietic cell tumor is a B-cell malignancy.

9. The method of claim 1, wherein the hematopoietic cell tumor is selected from the group consisting of a myeloma, a lymphoma and a leukemia.

10. The method of claim 1, wherein the donor's hematopoietic cells are bone marrow cells.

11. A composition comprising purified hematopoietic cells primed to produce an effector T cell immune response to a foreign tumor specific antigen, wherein the tumor specific antigen comprises an immunoglobulin idiotype.

12. The composition of claim 11, wherein the immunoglobulin idiotype further comprises the entire immunoglobulin molecule.

13. The composition of claim 11, wherein the immunoglobulin idiotype is an IgG kappa.

14. The composition of claim 11, wherein the hematopoietic cells are bone marrow cells.

15. A method of treating a hematopoietic cell tumor by the transplantation of hematopoietic cells from a human donor to an allogeneic recipient to enhance cellular immunity to treat the hematopoietic cell tumor in the recipient comprising:
   a. immunizing the donor's hematopoietic cells with an antigen specific for the recipient's hematopoietic cell tumor; and
   b. transplanting the donor's immunized hematopoietic cells directly to the recipient, such that an antigen specific effector T cell immune response to the hematopoietic cell tumor is transferred to the recipient, the donor's transplanted and immunized hematopoietic cells thereby treating the hematopoictic cell tumor in the recipient.

16. A method of improving a transplantation of hematopoietic cells from a human donor to an allogeneic recipient to enhance cellular immunity to treat a tumor in the recipient comprising:
   a. immunizing the donor's hematopoietic cells with an antigen specific for the recipient's tumor; and
   b. transplanting the donor's immunized hematopoictic cells directly to the recipient, such that an antigen specific effector T cell immune response to the tumor is transferred to the recipient, the donor's transplanted and immunized hematopoietic cells thereby improving the transplantation of the hematopoietic cells to treat the tumor in the recipient.

17. A method of treating a tumor by the transplantation of hematopoietic cells from a human donor to an allogeneic recipient to enhance cellular immunity to treat the tumor in the recipient comprising:
   a. immunizing the donor's hematopoietic cells with an antigen specific for the recipient's tumor; and
   b. transplanting the donor's immunized hematopoietic cells directly to the recipient, such that an antigen specific effector T cell immune response to the tumor is transferred to the recipient, the donor's transplanted and immunized hemopoietic cells thereby treating the tumor in the recipient.

* * * * *